United States Patent [19]

Alfano et al.

[11] Patent Number: 5,371,368

[45] Date of Patent: Dec. 6, 1994

[54] ULTRAFAST OPTICAL IMAGING OF OBJECTS IN A SCATTERING MEDIUM

[76] Inventors: Robert R. Alfano, 3777 Independence Ave., Bronx, N.Y. 10463; Ping-Pei Ho, 24 W. Terrace Rd., Great Neck, N.Y. 11020; Leming Wang, 49-45 175th Pl., Flushing, N.Y. 11365

[21] Appl. No.: 920,193

[22] Filed: Jul. 23, 1992

[51] Int. Cl.5 ............................................. G01N 21/49
[52] U.S. Cl. .............................. 250/341.1; 250/358.1; 128/664
[58] Field of Search ............................ 250/341, 358.1; 128/664, 665

[56] References Cited

U.S. PATENT DOCUMENTS

| | | | |
|---|---|---|---|
| 4,174,524 | 11/1979 | Moran | 358/95 |
| 4,707,128 | 11/1987 | Coles | 356/4 |
| 4,807,637 | 2/1989 | Bjorkholm | 128/664 |
| 4,945,239 | 7/1990 | Wist et al. | 250/358 |
| 4,948,974 | 8/1990 | Nelson et al. | 128/664 |
| 5,140,463 | 8/1992 | Yoo et al. | 250/486.1 |

OTHER PUBLICATIONS

Wang et al, "Ballistic 2-D Imaging Through Scattering Walls Using an Ultrafast Optical Kerr Gate", Science, vol. 253 pp. 269–271, Aug. 16, 1991.
Maarek et al., "Simulation of laser tomoscopy in a heterogeneous biological medium," Medical & Biological Engineering & Computing, vol. 24, pp. 407–414 (Jul. 1986).
Andersson-Engels et al., "Time-resolved transillumination for medical diagnostics," Optics Letters, vol. 15, No. 21, pp. 1179–1181 (Nov. 1, 1990).
Alfano et al., "Photons for prompt tumour detection," Physics World (Jan. 1992).
Wist et al., "A Light Imaging Technique for the Improved Detection of Breast Cancer," published at the Eighth Southern Biomedical Engineering Conference, Richmond, Virginia (Oct. 15–16, 1989) pp. 45–49.

*Primary Examiner*—Paul M. Dzierzynski
*Assistant Examiner*—Drew A. Dunn
*Attorney, Agent, or Firm*—Kriegsman & Kriegsman

[57] ABSTRACT

A system for imaging an object in or behind a highly scattering medium includes a laser for illuminating the highly scattering medium with a beam of light. The light emerging from the highly scattering medium consists of a ballistic component, a snake-like component and a diffuse component. A 4F Fourier imaging system with a Kerr gate located at 2F is used to form a time-space gated image of the emerging light, the time-space gated image consisting primarily of the ballistic component and the snake-like component.

9 Claims, 14 Drawing Sheets

λ=830-nm

λ=670-nm

VIEW FROM LEFT EYE     VIEW FROM RIGHT EYE

ULTRAFAST OPTICAL IMAGING OF OBJECTS IN A SCATTERING MEDIUM

BACKGROUND OF THE INVENTION

The present invention relates generally to imaging methods and systems useful in the detection of hidden objects in turbid, i.e. scattering media and more particularly to a novel imaging method and system of the type described above having improved spatial resolution characteristics.

Recent cancer statistics (NIH publication No. 89-2789) indicate that breast cancer has the highest incidence rate (337.4/100,000) and the highest mortality rate (95.2/100,000) of any cancer in the United States since 1973. At present, early detection of breast cancer offers the best hope for improving the survival rate. X-ray mammography is the most common and currently the most reliable diagnostic tool for quantitatively diagnosing breast cancers. Despite its well-demonstrated usefulness, mammography has some important drawbacks: (1) ionizing radiation (x-rays) is utilized for imaging the breast—such radiation may be a cause of breast cancer induction, Particularly with women having an AT-gene, and/or may pose a radiation risk to young women of child bearing age; (2) images of dense of thick breasts are difficult to obtain; and (3) small growths, i.e., 1 millimeter or less, in the early stages of cancer cannot easily be detected.

Transillumination is another technique which may be used to image breast tumors. In transillumination, visible light is incident on one side of the breast and a shadow image of the tumor is recorded on the opposite side. However, the ability to observe an image thus formed is severely limited by light scattering in the breast, which reduces the intensity of the unscattered light used to form the image shadow ant contributes to noise. The reduction of the unscattered light with respect to the scattered light limits transillumination as a viable technique with which to detect breast cancer to a spatial resolution greater than 1 cm. Consequently, when a tumor is either very small (e.g. a few millimeters) or lies deep inside a breast, it may not be observed by transillumination.

To improve the detectability of small tumors located inside a breast using transillumination, one must separate the unscattered light from the scattered light. This may be done by exploiting the properties of photon migration through a scattering medium. When photons migrate through a turbid medium, there are three main signal components: (1) diffusive (incoherent) photons; (2) ballistic (coherent, forward-scattered) photons that arrive first by traveling over the shortest path; and (3) snake (quasi-coherent) photons that arrive within the first dt after traveling over relatively short paths. The diffusive scattered photons of the signal travel over a much larger distance in turbid samples than the ballistic or snake photons, which take shorter paths through the medium within a small forward angular cone. It is believed that the ballistic and snake components contain the least distorted image information and that the diffusive component loses most of the image information.

Therefore, to see through a random medium, one should selectively detect the ballistic and snake-like photons, which contain information about the object, and reject diffuse photons, which only contribute -noise. This process of selection and rejection has been done using various time-resolved techniques (see, e.g., Delpy et. al., Phys. Med. Biol., Vol. 33, 1433 (1988); Yoo et. al., Appl. Opt., Vol. 28, 2344 (1989); Hoet et. al., Appl. Opt., Vol. 28, 2304 (1989); Yoo et. al., Opt. Lett., Vol. 15, 276 (1990); Hebden et. al., Appl. Opt., Vol. 30, 788 (1991); Andersson-Engels, Opt. Lett., Vol. 15, 1179 (1990); Spears et. al., IEEE Trans. Biomed. Eng., Vol. 36, 1210 (1989); and Rebane et. al., Nature Vol. 351 378 (1991) ).

Other patents and publications of interest include U.S. Pat. No. 5,140,463 to Yoo et. al., issuing August 18, 1992 (U.S. patent application Ser. No. 07/489,942 filed Mar. 8, 1990); U.S. Pat. No. 4,945,239 to Wist et. al., issued Jul. 31, 1990; Wang et. al., Science, Vol. 253, 769 (1991); Alfano et. al., Physics World, 37 (January 1992); and Wist et. al., "A Light Imaging Technique for the Improved Detection of Breast Cancer," Eighth Southern Biomedical Engineering Conference, Richmond, Va. (Oct. 15–16, 1989).

SUMMARY OF THE INVENTION

It is an object of the present invention to provide a novel imaging technique useful in the detection of hidden objects in turbid, i.e., scattering media, It is another object of the present invention to provide a transillumination imaging technique that can be used to detect objects in the submillimeter range.

It is still another object of the present invention to provide a transillumination imaging technique as described above which can be used to obtain 2-dimensional (2-D) and 3-dimensional (3-D) images.

According to one feature of the present invention, a Kerr gate is used to temporally gate the light exiting the transilluminated medium. The Kerr gate, which is controlled by a pump beam of light, opens for an appropriately short period of time to permit the ballistic and snake components of the light exiting the medium to pass therethrough for imaging and then closes to prevent the diffuse component of The light from passing therethrough.

According to another feature of the present invention, a 4F Fourier gate is additionally used to spatially gate the light exiting the transilluminated medium. The 4F Fourier gate improves image quality by filtering out the component of light exiting the medium at large angles i.e., the diffuse component. In a preferred embodiment of the invention, the Kerr gate and the 4F Fourier gate are combined by placing the Kerr gate at the 2F spectral plane and by gating only that portion of the Kerr gate situated at the focal point of the 4F Fourier system.

As can readily be appreciated, one application of the present invention is in the detection of breast tumors.

Additional objects, features and advantages of the present invention will be set forth in part in the description which follows, and in part will be obvious from the description of may be learned by practice of the invention. In the description, Preference is made to the accompanying drawings which form a part thereof and in which is shown by way of illustration specific embodiments for practicing the invention. These embodiments will be described in sufficient detail to enable those skilled in the art to practice the-invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF PREFERRED EMBODIMENTS

Figure 1:
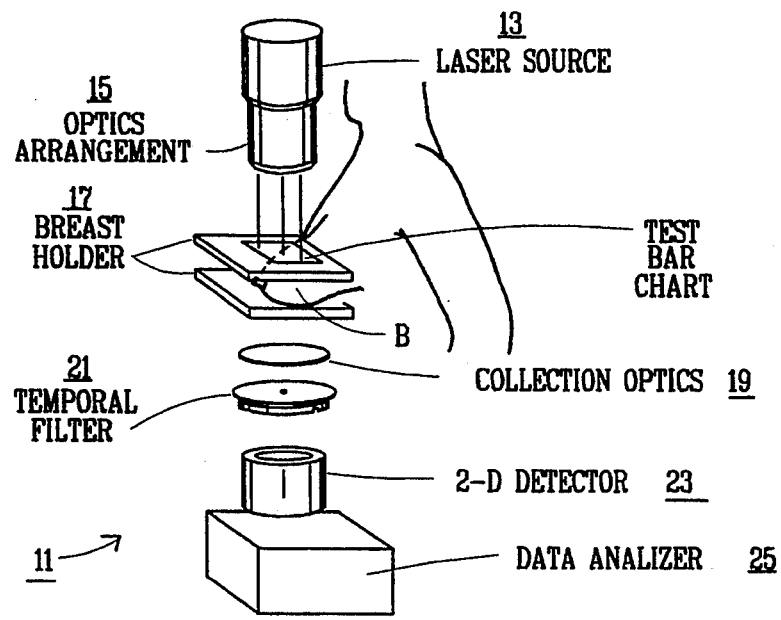
FIG. 1 is a schematic diagram of picosecond time-space gated optical breast imaging system according to this invention.

The ultrafast time-space gate imaging technique of this invention may be used as an example to detect hidden objects and disease tissues in biomedical media, such as chicken tissues, human breast tissues, and human breasts and organs in-vivo. This time-space gated optical imaging may serve to revolutionize optical mammography as a cancer screening tool. Using two gates in parallel or one gate with. alternative sequence at two different angles, two images from early arrival signals can be obtained and reformed into a 3-D snake/ballistic stereoscopic image. The significance of the time-space gated optical imaging approach for the breast cancer screening will be:

a) a safe non-ionizing radiation diagnosis technique;

b) an early detection of abnormal tissues with improved spatial resolution;

c) a spatial gate to remove higher spatial frequency noise signals;

d) a method to distinguish malignant and non-malignant tissues in vivo using different wavelengths of light to illuminate the tissue; and e) a 2-D and 3-D monitoring method using video systems for surgeons who perform surgical operations in real time for improved accuracy and effectiveness.

Key points of this invention include:

a) 2-D imaging using time-gated ballistic/snake signals with gating time from 100-fs to 50-ps;

b) The additional Fourier spatial gate with the time gate. The spatial aperture can be obtained with the time-gating laser beam profile;

c) The use of differential absorption cross sections from multiple wavelengths probing to identify the states of disease;

d) The use of two 2-D time-gated ballistic/snake disparity images 3-D stereoscopic imaging.

e) The use of static and induced-spatial gate to remove higher spatial frequency optical components;

f) The use of 4F imaging system of Fourier-plane-Kerr-gate to collect ballistic/snake early arrival signals; and g) The use of near IR laser sources from 800-nm to 1350-nm using mode-locked Ti:sapphire, semiconductors, Forsterire, and YAG lasers.

Optical detection and imaging methods have been used in the past to determine ultra-small hidden objects in turbid and bio-medical medis. For example, steady-state transillumination (diaphanography) provides a direct visual interpretation for breast examinations but limited ≧1-cm resolution due to scattering. Optical signals transmitted through the breast depends on the size, amount of fat, composition and optical density of skin and glandular tissues, vascular supply, and the presence and extent of fibrosis, inflammations, cysts, and neoplasia. With the advancement of ultrashort lasers and ultrasensitive detectors, a ~10-μm spatial resolution of the optical image in a turbid medium can be achieved. Recently, based on the time-resolved imaging which restricts detection to the earliest living photons, the spatial resolution of a 1-ps time- gated image through a 5-cm thick human breast is estimated to be ~1-mm. Using the available parameters transport mean free path =3-mm, absorption length =100-mm) of tissues, the calculated total transmitted ballistic/snake light through a ~5-cm thickness of breast is about $10^{-10}$. From a theoretical analysis, the calculated transmitted ballistic/snake signal indicated the photon fluence of $2 \times 10^{-16}$ #/$\mu$m2 can be obtained from a 5-cm thick breast. Given the input laser power to be 1-mW, for a one second exposure time, $3 \times 10^5$ photons should be detected in 1-mm2 area. Using the-state-of-the-art detection devices with high temporal resolution and low level detection capabilities, an improved picosecond optical. Kerr gate as per this invention can be used to image thick turbid, i.e., scattering, biomedical media.

Figure 2:
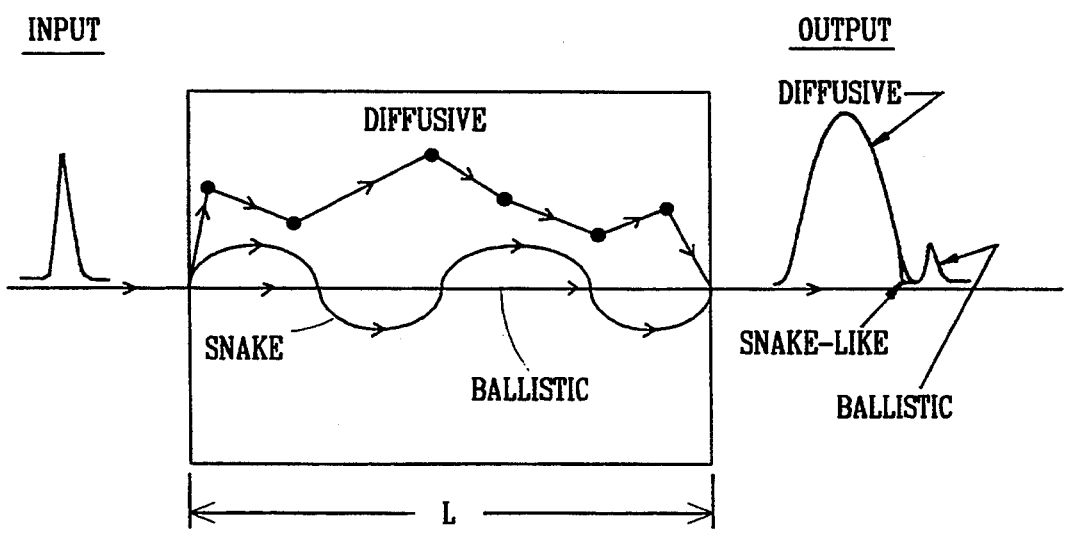
FIG. 2 is a schematic showing ballistic, snake and diffusive signals of a pulse propagating through a turbid medium.

When photons migrate through a turbid medium, there are three main signal components: diffusive (incoherent) and ballistic (coherent), and snake (photons which arrive within the first δt after traveling over some shorter paths). The diffusive scattered photons of the signal travel over a much larger distance in turbid samples, while the ballistic one takes the shortest path through the medium within a small forward angular cone. The snake component arrives on the onset of diffusive component. In a highly scattering inhomogeneous medium, such as tissues, human breast, the contribution to the ballistic component becomes small and merges into the diffusive component. In our case, we select the earliest arrival signal within the first 10- ps called tine snake component. A schematic diagram of pulse propagation in turbid media is shown in FIG. 2. The ballistic component and the snake component preserve image information while the diffusive component loses most of information.

Time-resolved techniques can be used to separate-out the ballistic and snake components from the diffusive component of light migration turbid media. A schematic of the time-gated ballistic/snake breast imaging system is shown in FIG. 1 and is represented generally by reference numeral 11. As can be seen, system 11 includes a laser source 13, an optics arrangement 15 for focusing the light emitted by laser source 13, a breast holder 17 for holding a breast B to be tested, optics 19 for collecting the light passed through breast B, a temporal filter 21 (such as a picosecond ker gate) for selectively passing the ballistic and snake components of the light passed through breast B, a 2-D light detector 23 for detecting the ballistic and snake components passed through filter 21 and a data analyzer 25.

Figure 3:
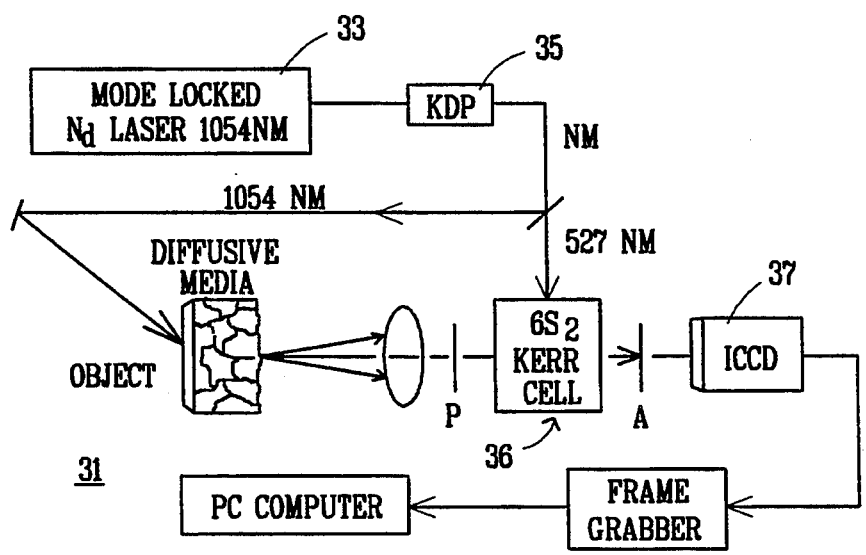
FIG. 3 is a schematic of a 2-D picosecond optical Kerr imaging system.

A schematic of an experimental picosecond Kerr gate imaging system acccording to this invention is shown in FIG. 3 and is represented generally be reference numeral 31. It consists of a mode -locked Nd:glass laser 33, a KDP crystal 35, a CS2 Kerr gate 36 and a 2-D readout system 37. The laser pulse has a peak power of $5 \times 10^8$-W, duration time 8-ps, and wavelength 1054-nm. The pulse energy is ~4-mJ. The 1054-nm laser beam is sent through KDP crystal 35 to produce the second harmonic component with the wavelength 527-nm, a peak power of ~$10^7$-W, and a beam diameter of ~1-cm, which is the probing source illuminate the hidden object. The typical transmission efficiency of a CS2 Kerr shutter is ~10%. The image was recorded by a 2-D image intensified CCD (ICCD) camera with 640×480 pixels, 6000 times gain and dynamic range 100:1. Its minimum detection level is ~1 Lux/cm2 (104 photons/mm2). A PC computer, a frame grabber, software package, and video printer are used to store, process, and display the images.

Figure 4:
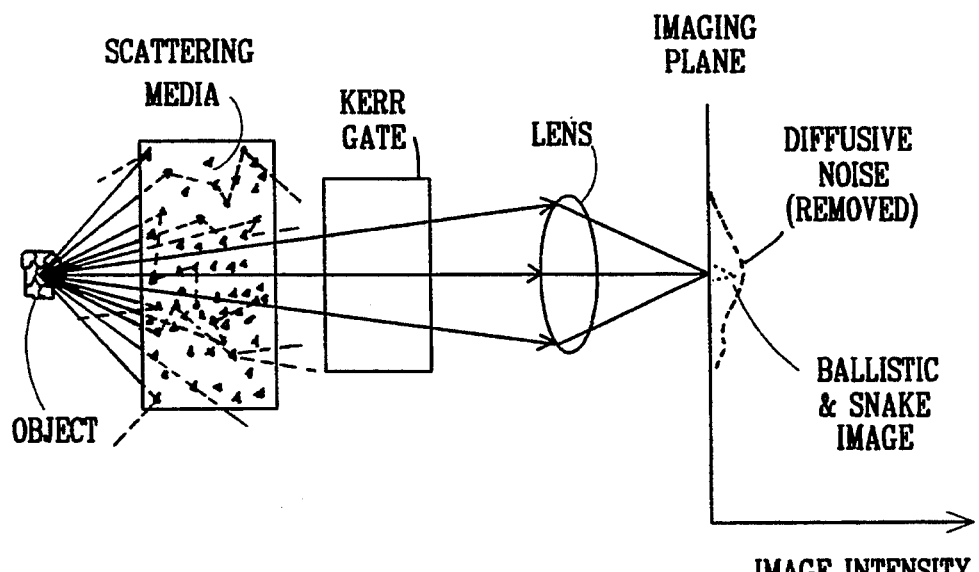
FIG. 4 is a schematic of image ballistic (and snake) and diffusive light using an ultrafast Kerr gate.

Various hidden objects in turbid media were measured using this Kerr gate system to separate the ballistic and snake images from the diffusive noise. FIG. 4 displays the images of ballistic and diffusive components from a point source within/behind a turbid, i.e., scattering medium. The scattering medium consisted of polystyrene spheres of diameter ~0.46-um suspended in water solution in an optical cell with the dimension $5 \times 5 \times 5$ cm$^3$. The volume density of spheres was 0.88% for all measurements except in the double-quasi-point source measurement where the density was 0.3%. The calculated scattering coefficient was $n\text{O}2 \sim 21.7$ for single point source and Bar chart and $n\text{O}2 \sim 21.7$ for the double-quasi-point fluorescence imaging test, where n is the number density of scattering particles, $\sigma$ is the scattering cross section, and z is the thickness of the sample. The Kerr Gate image intensity for single point source and the Bar chart in a scattering medium have been measured as a function of delayed gating time. The ballistic (and snake) signal corresponds to intensity located at a gating time of about T=0 to 10-ps. The peak of the diffusive component follows the ballistic signal and appeared at ~20ps. This is consistent with the model presented in FIG. 2.

Figure 5:
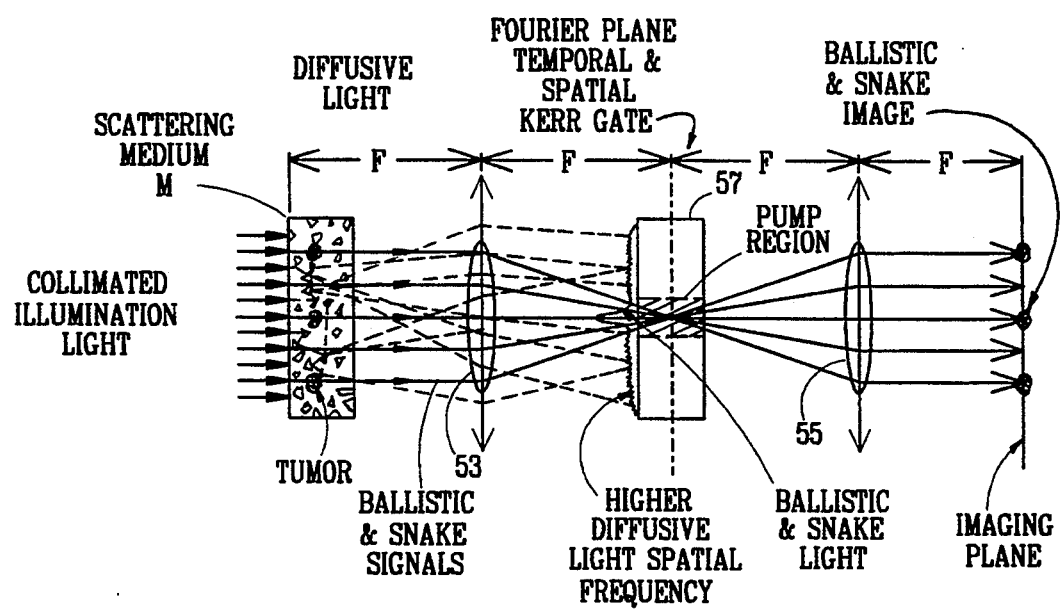
FIG. 5 is a schematic illustrating time-space gated imaging according to this invention.
Figure 6A:
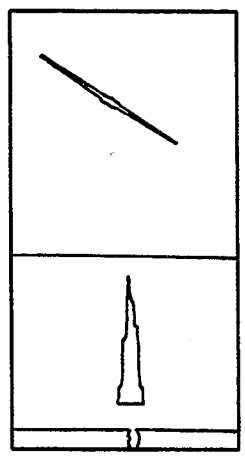
FIGS. 6A, 6B, 6C and 6D are images of a single-point source in a diffusive media for four different gating times.
Figure 6B:
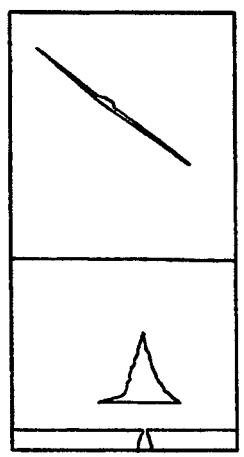
Figure 6C:
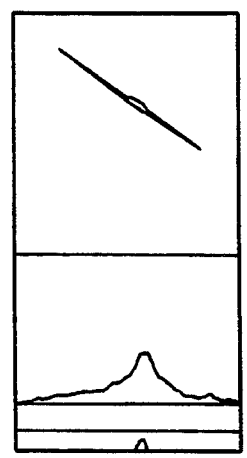
Figure 6D:
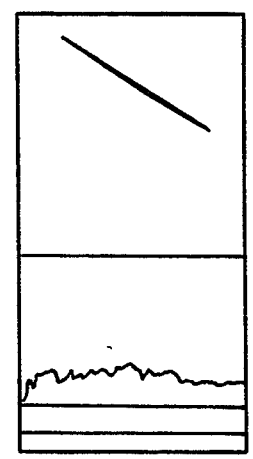

A 4F Fourier image system with the time Gate located at 2F according to this invention is displayed in FIG. 5. The system includes a laser (not shown) for Generating a laser pulse, a pair of lenses 53 and 55 and a Kerr gate 57. The transmitted signal from a collimated incident. laser pulse through a scattering medium M located at the focal plane of the first lens 53 is spatial-filtered. Higher spatial frequency components will be removed from the time-gated images collected at the 4F image plane. Better S/N can be obtained.

Four types of hidden objects in turbid media were measured:

(a) Single-Point Source

The time-gated images of the single 200-$\mu$m point source at different gating times are displayed in FIG. 6 as 2-D video photographs with their corresponding densitometer traces. The size of the image changes at different gating times. The image resolution decreased when the gating time delay was increased from time T=0. At the ballistic time T=0, the 200-$\mu$m image spot size was resolved (shown in FIG. 6a1). At T=40-ps, no image information was observed in FIG. 6d. It is clear that image information is retained in the ballistic component of the transmitted signal light not in the diffusive component.

Grid Behind A 4-cm Intra-Lipid Solution

Figure 7A:
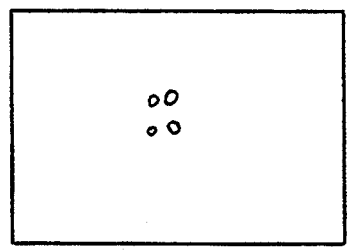
FIGS. 7A, 7B, 7C and 7D are time-resolved Transillumination Kerr images of 8-ps 530-nm laser pulse propagated through a grid (200um×300um) in front of a 4-cm thick intra-lipid solution at different times. (a) $T_D$ =0-ps (b) $T_D$ =13.3-ps (c) $T_D$ =30-ps (d) Reference (no turbid medium)
Figure 7B:
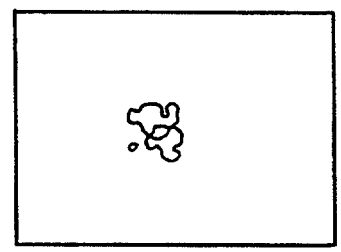
Figure 7C:
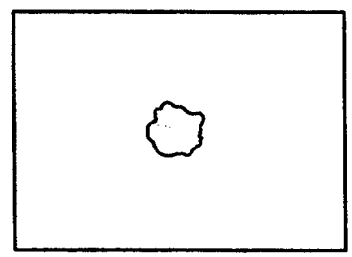
Figure 7D:
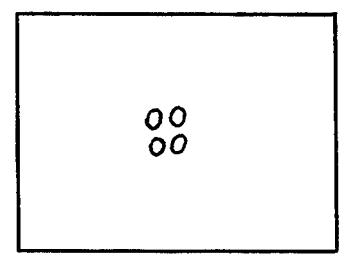

Images of a grid through a 4-cm thick 0.05% intra-lipid solution is resolved by the Kerr gate as shown in FIGS. 7a, 7b, and 7c. A 0.5% intra- lipid solution has the similar scattering property as the human breast. FIG. 7d is the reference image of the grid through air. The width of the black line is 200-$\mu$m and the width of white dots is 300-$\mu$m. In FIG. 7a, the ballistic (TD=0) image of the grid is shown in FIG. 7a. 2-D grid .,image has been clearly resolved. In FIG. 7b, the snake (TD=10-ps) image of the grid is blurred. When TD=30-ps, the image shown in FIG. 7c is distorted from the late arrived diffusive light.

(c) Bar Chart Behind A 3.5-mm Human Breast Tissue

Figure 8A:
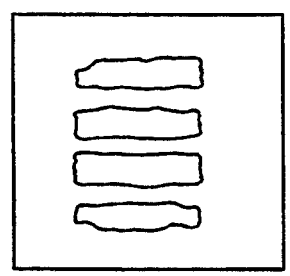
FIGS. 8A and 8B are time-resolved Kerr images of a test bar chart behind a 3.5-mm human breast tissue in vitro. The width of the bar is 100-um. (a) $T_D$ =0-ps and (b) No gate.
Figure 8B:
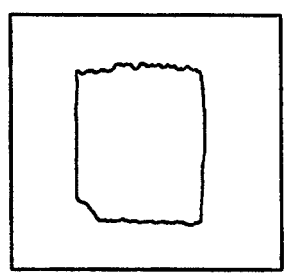

Images of the Bar chart through a piece of 3.5mm thick human breast tissue is displayed in FIG. 8. Due to the large diffusive noise, the image without the gate was totally blurred as shown in FIG. 8b. No clear image can be observed from the conventional transillumination approach. With a time gate at T=0-ps, a clear 100-$\mu$m width bar image with contrast ratio=0.8 was obtained in FIG. 8c.

(d) Fish

Figure 9:
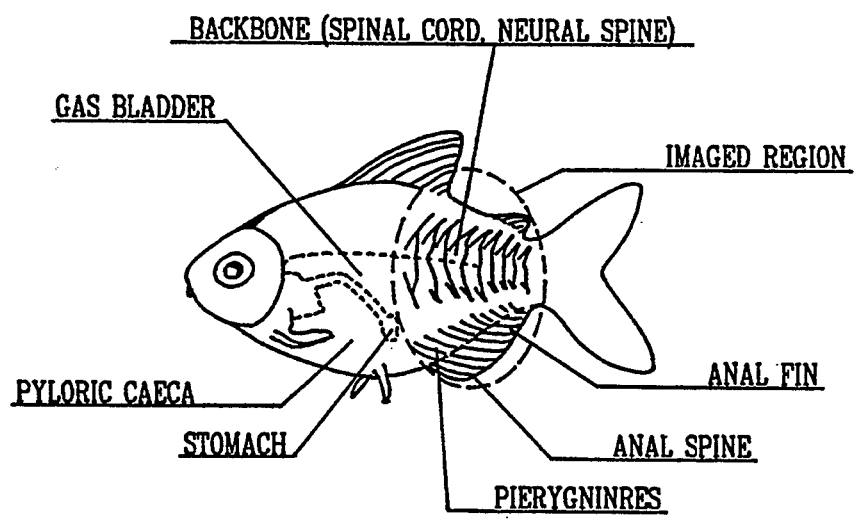
FIG. 9 is an anatomical illustration of a Tetra gold fish used in an experiment. The area within the thicker dashline was illuminated by 527-nm laser pulse. Time-gated images are shown in FIG. 10.
Figure 10A:
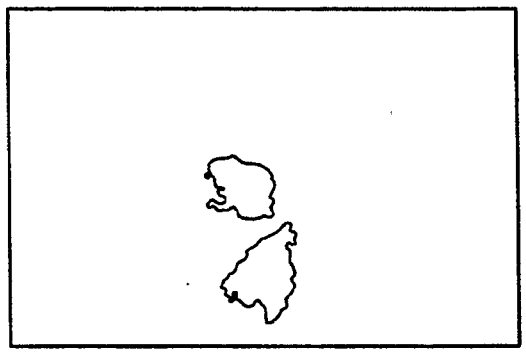
FIGS. 10A, 10B, 10C and 10D are picosecond Optical Kerr Gated images of the gold fish in vivo (a) an image gated at T=6.6-ps; (b) an image gated T=16-ps; (c) an image gated at T=30-ps; (d) an image gated at T=40-ps. The time T=0 is defined to be the time when the laser pulse passes through the vertical geometrical plane without the fish.
Figure 10B:
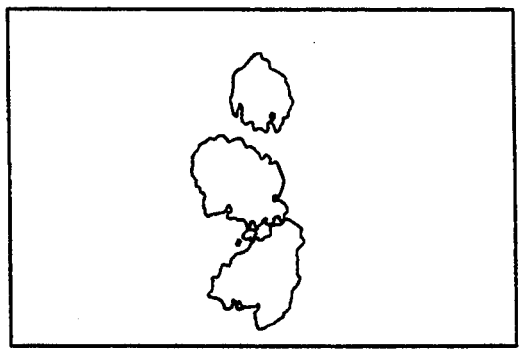
Figure 10C:
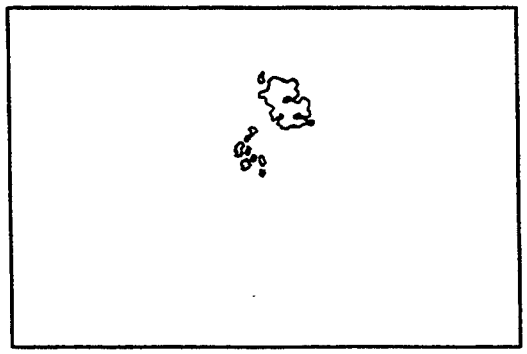
Figure 10D:
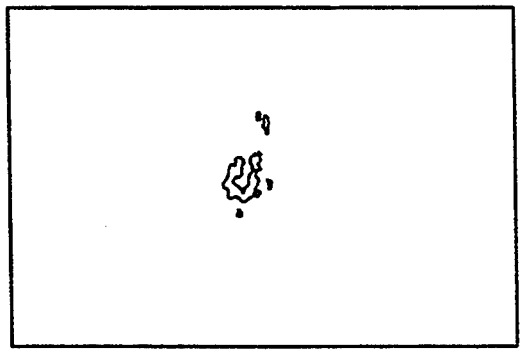

A 532-nm laser pulse with the spot size ~6-mm was used to illuminate the back portion of a Tetra gold fish shown in FIG. 9. The fish was ~4-mm in thickness, ~25-mm in length, and ~12-mm in width image the interior of a fish body to show internal anatomical structure, a series of time-resolved transillumination images of the fish were measured in vivo at four different gating times as shown FIG. 10. The forward scattering ballistic image light was Kerr time-gated and detected by an ICCD camera. Four Kerr time-gated transillumination images of rear part (without tail) of the fish are displayed in FIG. 10. Due to the inhomogeneity of fish material distribution and thickness variation, these time-resolved ballistic images are complex. In FIG. 10a, transmitted signals from the fish ventral fin and pteryiophores are shown at T=6.6-ps. The time T=0 is defined to be the time when the laser pulse peak passes through the vertical geometric plane without the fish. A clear image of the fish ventral fin because the fin is very thin. The time for the laser pulse to pass through the fin is almost the same as for the light that propagates in air. From the earliest detected ballistic image, the interior of the fish pterygiophores in FIG. 10a has the highest This backbone portion was thicker and the refractive index was larger. The laser pulse took a longer time to pass through the bone and be time-rated out. The image shown in FIG. 10b is brighter than all other photographs (FIGS. 1a, 10c, and 10d). In FIG. 10b, the transmitted laser light came out from the fish body, mostly from the backbone portion. It has the clearest image of the fish, backbone images shown in figs. 10c and 10d gated at later times were blurred by diffusive scattering light noise from other parts of fish. In these two pictures obtained from later times, no clear image information of the fish body were obtained.

In our previous analysis of time-gated optical imaging for imaging ga thick biomedical sample higher S/N ratio ($>10^{10}$) and shorter opening time (~1ps) are needed. A cascaded double-stage optical Kerr gate (DOKG) system can improve the S/N and the gating time. An improvement of ~500 times in S/N has been achieved over that of a single-stage optical Kerr gate (SOKG) system. The gating time of a DOKG was 3 times faster.

Figure 11:
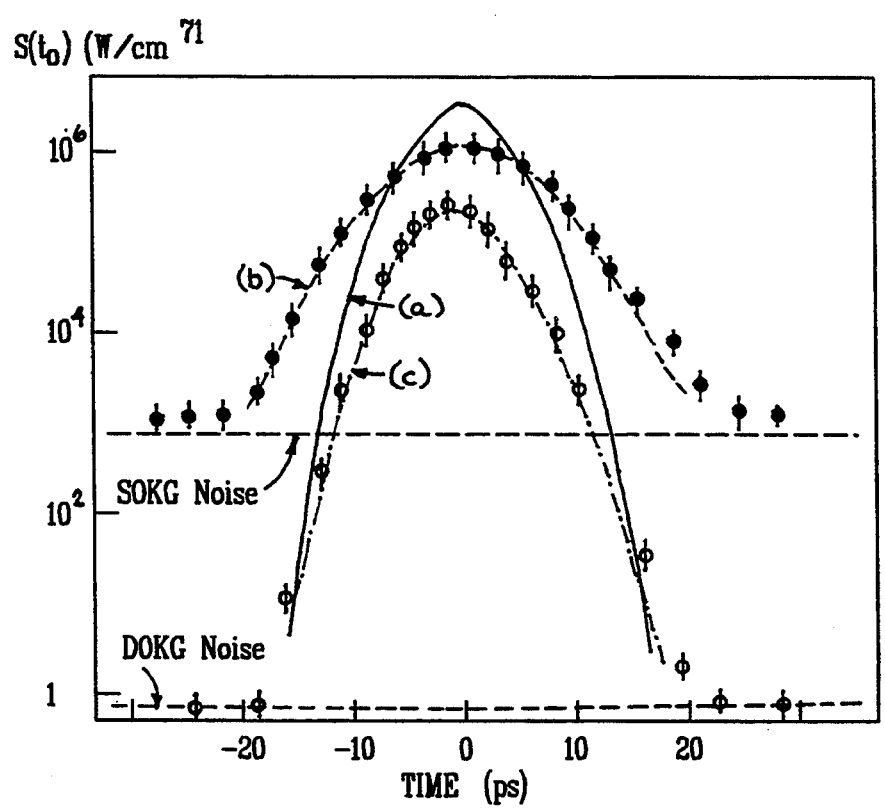
FIG. 11 is a graph of gated transmitted signals as a function of gating time $T_D$ for a SOKG(*) and a DOKG(O)

The DOKG setup is described below. A mode-locked Nd:glass laser which emitted pulses with a wavelength 1054-nm and 10-ps duration was used as the gating source. The peak intensity of the Kerr gating pulse was adjusted from ~0.1 to 2 GW/cm2. A potassium dihydrate phosphate crystal was used to produce the second harmonic generated pulse (SHG) for probing. In a DOKG, the 1054-nm beam was split using a 50/50 mirror into two shutter beams. These beams were passed through two Kerr gates with independent time control. The shorter gating time was achieved in a DOKG, due to the non-synchronized overlapping of two independent gating times. Two types of DOKG were studied: when the two gating times can be either the same or different. When their gating times are equal, this DOKG is called the synchronized double-stage optical Kerr (SDOKG). While for different gating times, this DOKG is called the non-synchronized double-stage optical Kerr gate (NDOKG). The improvement in S/N for the DOKG system arises from the reduction of the noise, mainly, the leakage from inferior crossed polarizers. The maximum S/N for a SOKG system was $1.5 \times 10^3$ which was limited by ($\sim 2.5 \times 10^3$. For an DOKG system, the S/N was $5 \times 10^5$ which was limited by $\sim 7 \times 10^5$ of a cascaded two pair crossed polarizers. The gating times from SOKG and NDOKG has been measured as a function of the delayed probing time to and non-synchronized gating times st. For the NDOiKG, e-1 decay time of the gated transmitted signal was $\sim 5.6$-ps at $\delta t = 11$-ps and 1-GW/cm2 gating intensity. This value is a face better than SOKG. The transmitted curves from a SOKG and a NDOKG are shown in FIG. 11.

The gate decay times have been obtained by selecting the time from the peak of calculating Kerr intensity profile drops to its e-1 value. These calculated delay times at different pump pulse intensities fitted with the measured gating times. The gating times of SOKG increase with the gating power. The reduction of gating time of NDOKG is due to the overlapping of two fast oscillating gates. The transient gating time of the interaction function depends on the partial overlap of two fast sinusoidally time oscillating functions as a function of intensity. After deconvolution of the integrated gate decay time displayed in FIG. 11c, the transient gating time of the NDOKG is even faster (~1-ps), When the intensity increases, the transfer function becomes broadened and oscillating for both SOKG and DOKG, but becomes narrower for the NDOKG. The dramatic change of the temporal distribution for the NDOKG in comparison to the other gates is due to the non-synchronized overlapping of two induced phase shifts in two Kerr cells. The partial overlapped in time from these two oscillating Kerr gates leads to significant reduction in the overall system gating time. Due to the convolution of probing pulse and nonlinear Kerr response function, the temporal width of the transient probing pulse is directly proportional is much narrower than the integrated transmitted signal. The transient gating width from the given NDOKG is 3.3 times faster than that of the input laser gating pulse. X-ray mammography, sonography, thermography, nuclear magnetic resonance, and diaphanography (optical transillumination) are several existing techniques for breast imaging. Optically, in the conventional diaphanography or transillumination, direct visual interpretation or IR mapping from video imaging is used which provides an extension of physical examinations of the best. In this method, both the ballistic, snake, and diffusive signals are detected without a time-gate which results in higher noise levels and poor spatial resolution($>$1cm). Knowledge of photon migration in the time-domain can significantly improve the contrast and resolution of optical images as shown in our preliminary work.

Using optical techniques, especially, ultrashort lasers and time-gating, several new optical techniques for breast imaging and computer-assisted optical tomography have been investigated. Chance et all has demonstrated an optical imaging system using the streak camera technology to study the deoxyhemoglobin in brain with a simulation system. A preliminary study of optical range tomography using a streak camera has been demonstrated. Poor spatial resolution is the key issue in the use of streak camera 2-D imaging method. The gain from the stimulated Raman scattering was used to enhance the quality of optical images in scattering media. Chrono-coherent imaging (CCI) was performed using the principle of pulsed holographic interference technique. A holographic image is formed from the coherent (ballistic) part and is separated out from the incoherent (diffusive) part which takes a longer path and contributes a uniform noise background. In order to separate out the ultra-large dc background from the diffusive light, a large dynamic range of detector is required in CCI imaging which limits its capability. Time-resolved holographic techniques have been further studied using a polymeric film and using electronic video recording. Based on the coherent requirement for the time-resolved holographic technique, there is no need to setup an additional time gate for the ballistic signal imaging. However, the interference from the snake signal may not be available due to the loss the coherence through scattering. In a highly scattering medium, the ballistic signal may be too weak to be detected. Second harmonic nonlinear correlation detection has been performed by us which offers the highest S/N. A factor of e-32 attenuation of femtosecond input signal through turbid has been detected. This technology offers the highest possible S/N. It may be difficult to obtain a clear phase-matched 2-D images and only coherent ballistic components can be detected. Imaging techniques using continuous-wave lasers with absorption and fluorescence-absorption techniques have been tested by certain researchers. Images may be reconstructed through the inverse scattering approach. The disclosed time gate technique offers a mean to detect both ballistic/snake time-resolved 2-D and 3-D images with high S/N and spatial resolution.

Methods to be disclosed in this ultrafast time-gated transillumination imaging technique include three main sections: (A) improvements of our previously demonstrated Kerr gate imaging system, (B) improvements for system safety and accuracy, and (C) 3-D ballistic/snake imaging technique. Laser sources used in this technique include picosecond and femtosecond laser systems with wavelength spanned from 500-nm to 1500-nm. Mode-locked 8-ps glass laser system used for the preliminary study, fs colliding pulse mode-locked dye laser with a 20-W 10- KHz copper-vapor laser amplifier, fs YAG-dye laser system, mode-locked Ti:sapphire lasers, semiconductor diode lasers,and forsterire lasers will be examples to be used for the probing source for this disclosed technique. The time-gate will use ultrafast optical techniques and electronic gating approach.

In order to obtain a ballistic/snake signal through a 5-cm thick breast tissue with 1-mm spatial resolution, the S/N (removal of the long diffusive light) of the picosecond time-gate requires to be $\geq 10^{10}$. Several methods to improve the S/N of the time-resolved Kerr gate from the current value of $\sim 10^3$ to the desired value of $\sim 10^{12}$ will hereinafter be described.

Multi-Stage Kerr Gate

A cascade double-stage Kerr gate has increased the S/N by a factor of 500 times. Furthermore, due to the non-synchronized overlapping of two time-gates, the transient gating time has been reduced by 3 fold. In order to remove the long delayed diffusive noise component by a factor of $\sim 10^{12}$, a 5-stage gate with total $S/N=(S1/N1)^5) \sim (500)^5 \sim 3\times 10^{13}$ can be used. An alternative approach using the calcite polarizers will also be tested. The extinction ratio for a pair of crossed calcite polarizers is $> 10^6$. In this manner, S/N of $10^{12}$ may be obtained using a two-stage calcite Kerr gate system.

Spatial Filtering

Figure 12:
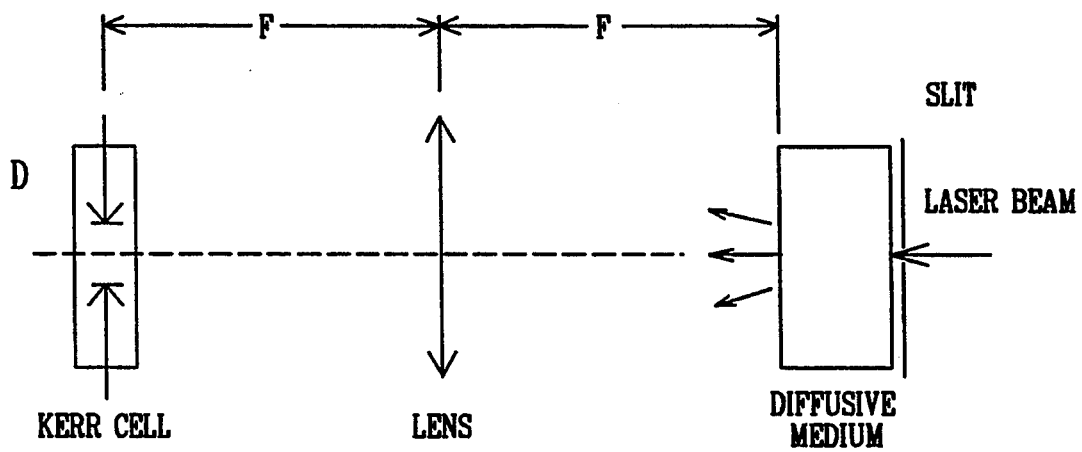
FIG. 12 is a schematic of picosecond gated Fourier spectral measurement.

Beside the time-gate, a space gate incorporated into the system will improve the image quality by eliminating large angle scattered diffusive noise. When a turbid medium is illuminated by a laser, there will be a diffractive pattern at the back focal plane. This is a Fourier spatial spectrum of the scattering medium. A schematic of experimental arrangement the picosecond Kerr gated Fourier spectral measurement is shown in FIG. 12. For an infinite large plane wave input light illumination, the highest spatial frequency which can be filtered through at the Fourier focal plane is $vs=D/(2F\lambda)$, where F is the focal length of the collection lens, D is the diameter of the aperture, and $\lambda$ is the illumination wavelength. For example, using an aperture at the gate: D=1-mm, illumination wavelength:$\lambda$=1-$\lambda$m, f=50-cm, all spatial frequencies higher than $vs=1mm/(2\times 1\lambda \times 50cm)=1/100\mu=10$ lines/mm.

Since the size of the random particles or tissues of the turbid medoa is $\sim 1-\mu$ to 40-$\mu$m (the corresponding spatial frequency is $\sim 1000$ to 25 lines/mm), most diffusive signals scattered from random particles or tissues are located at the higher spatial frequency spectral region on the spectrum plane (the further region from the center of the spectrum plane). This diffusive light can be (spatial-filtered out with a 10 lines/mm Fourier optical system. In addition, due to the increasing number of scattering and longer traveling path, high spatial frequency components arrive at the spectrum plane at the later time. Using a picosecond time gate, thins later arrived diffusive light can be further filtered out. By combining the spatial filter with an ultrafast time, the S/N of the imaging through turbid media can be greatly improved.

Figure 13A:
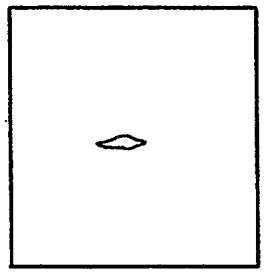
FIGS. 13A, 13B, 13C, 13D, 13E and 13F are graphs of time-resolved Fourier Spatialed Spectra.
Figure 13B:
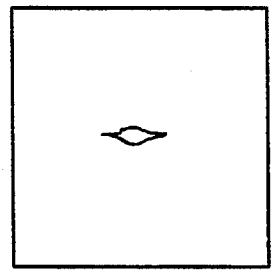
Figure 13C:
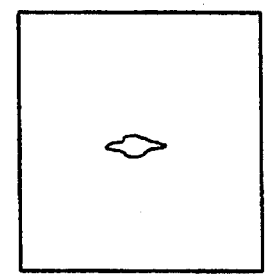
Figure 13D:
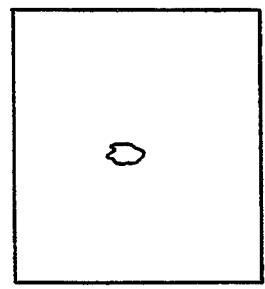
Figure 13E:
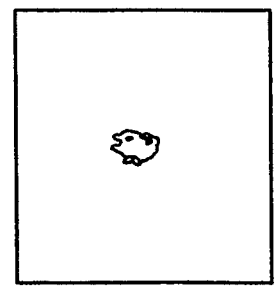
Figure 13F:
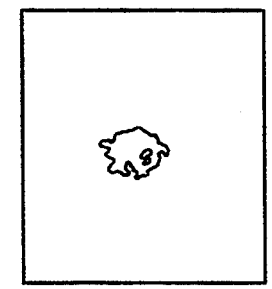
Figure 14A:
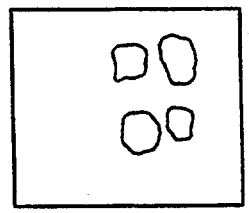
FIGS. 14A and 14B are transillumination images of a grid (200-um×300-um) through a 4-cm thick 1%intra-lipid solution using 5-mW lasers with wavelengths at (a) 830-nm; (b) 670-nm.
Figure 18A:
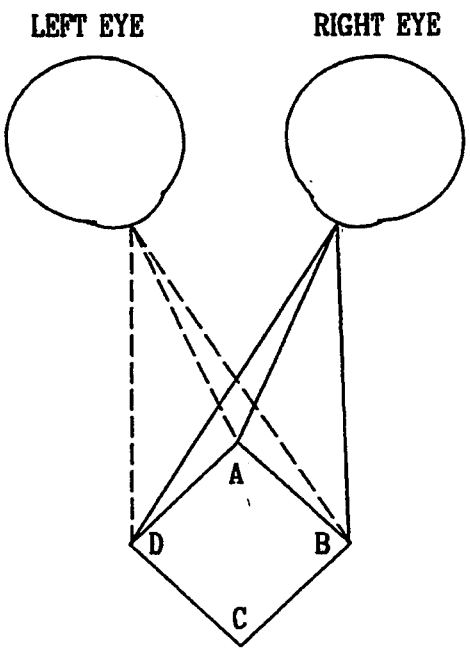
FIGS. 18A and 18B show how the two eyes looking at a cube see slightly different views of the cube.
Figure 18B:
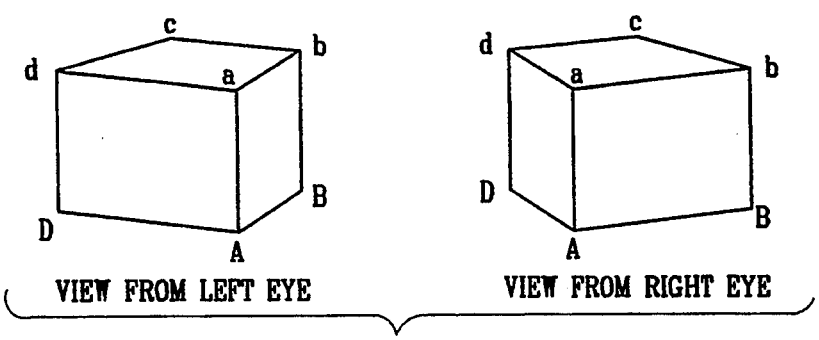

In order to transform the Fourier spatial filtered signal shown in FIG. 12 back to the true image, a 4F image system as shown in FIG. 5 is required. This is different to the conventional Kerr gate as shown in FIG. 4 where only time-gate is used. A time-resolved spatial filter system at the spectral plane built by an aperture-limited optical Kerr gate will be designed to study the improvement of S/N by rejecting most unwanted diffusive light. The diameter of the spatial filter is determined by the spot size of the pumping beam of the OKG. A preliminary result is shown in FIG. 13 The 530-nm pulse was illuminated through a grid (200-$\mu$m width) and imaged by an OKG. FIGS. 13a and 18b displayed the regular time-resolved grid image at gating time TD=0-ps and 20-ps, receptively. The ballistic signal at TD=0 was clearly resolved. FIGS. 14c and 14d displayed the time-resolved Fourier signals. The ballistic signal of FIG. 14c has a sharp-defined Fourier point signal at the center.

In addition, using a DOKG approach discussed above, S/N improvement can be obtained through the Kerr-gate spatial filtering. The second OKG is located at the imaging plane of the output of the illuminated signal from the first OKG. The S/N can be further improved by a factor of $> 10^4$.

(3) Cooled CCD Detection 2-D image intensified CCD camera was used before. The minimum detectability is about 0.01 Lux/cm2. A cooled CCD Camera system (500×500 pixels) will be used. In our test study, a test bar at the signal intensity of $\sim 10^{-15}$ W/cm2 can be detected For can input probing laser with intensity at $\sim 10^{-3}$ W/cm2, the cooled CCD has the capability to detect the ballistic/snake signal through a 5-cm thick breast tissue with a transmission factor of $\sim 10^{-12}$.

(4) Nonlinear Materials for Kerr Gate Liquid CS2 is commonly used for the nonlinear materials of a picosecond optical Kerr gate. The reorientational relaxation time of CS2 molecules is 1.8-ps. This limits the ultimation switching speed of the Kerr gate. Other nonlinear optical materials such as polymers and lead glass with high optical nonlinearity and faster switching speed ($<10^{-12}$) can be used for the Kerr medium of a imaging gate.

There is no known safety hazard to human tissues using red light under low energy density ($\sim$1-mJ/cm2) illumination. By comparing the data of an experimental study performed at Commonwealth University, Los Alamos Laboratory and NIH in 1974, the laser energy, peak power and peak intensity used in our proposed measurement are well within the safety limit for human beings. In their study, the threshold injury for the use of picosecond laser pulses directly illuminating the retina of monkeys in vivo was [67 GW/cm2 or $\sim$2J/cm2. The power density or energy density used in their measurement was $>1,000$ times than that of our measurement.

Under direct illuminaton, the laser pulse (energy density$\sim$20-mJ/cm2) for the Kerr gate may damage the eye. Standard laser safety procedures will be executed. The threshold power density (fluence) for the laser ablation of human tissues depends on the laser wavelength, cw or pulse operation, repetition rate, and types of tissues. The minimum threshold ablation power density is $>10$ J/cm2 for pulsed lasers and is $>100$ W/cm2 for continuous wave lasers. The power density of lasers and light sources proposed in our experiment is 1,000 times smaller than the known minimum damage threshold values of tissues. We propose the following techniques for use in improving the system safety and accuracy: probing wavelength, high repetition rate laser pulses, laser intensity, and single-ray scanning.

1) Wavelength Contrast Dependence

Figure 14B:
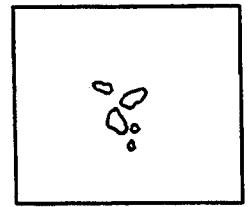
Figure 15:
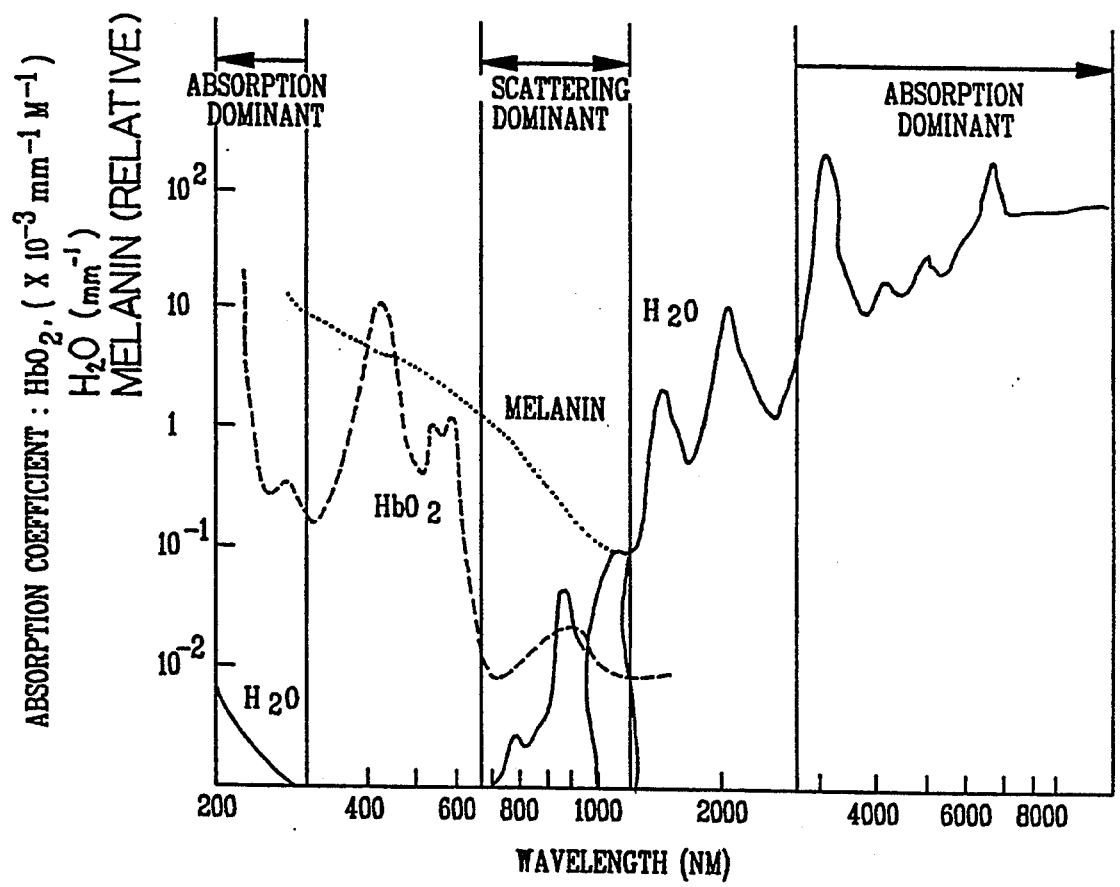
FIG. 15 is the absorption spectra of water, oxyhemoglobin: and melanin.

Due to the absorption from hemoglobin and other chromphores in breast tissues and other tissues, the wavelength dependence of scattering in turbid media, certain wavelengths used for the time-gated transillumination are better than the 530-nm laser pulse used in section 2.A. Using different wavelengths for the probe beam will enhance the necessary contrast to identify tumors and other defects in vivo. The steady-state transillumination images of a grid through a 4-cm thick 1% intra-lipid solution using 670-nm and 830-nm laser sources are displayed in FIG. 14a and 14b, respectively. From the $1/\lambda^4$ dependence of the Rayleigh scattering, the contrast of the grid image of FIG. 14b obtained from the longer wavelength laser is significantly better than that of the shorter wavelength laser. Wavelengths at 530-nm (second harmonic), 630-nm (stimulated Raman of 530-nm), and 750-nm (stimulated anti-Stokes Raman of 1060-nm) from mode-locked glass laser system, and 620-nm, 770-nm (stimulated Raman of 620-nm) from CPM femtosecond dye laser system will be studied. Furthermore, mode-locked Forsterire laser system is in operation in our laboratory. The operating wavelenth can be tuned from 1167-nm to 1350-nm with pulse duration from 0.5-ps to 30-ps. Due to the water absorption above $\sim$1300-nm, the tranmission spectrum in tissues varies significantly in this regime. The absorption spectra of water, oxyhemoglobin and melanin is shown in FIG. 15. The wavelengths in the region of 700-nm to 1350-nm will be ideal to penetrate through tissues for the imaging of thick biomedical samples.

2) Repetition Rate

The random noise at the CCD detector can be reduced as a function of the square root of the number, N, of signal pulse to be averaged. Using a 10-KHz copper-vapor laser amplified laser pulse with the energy 1-$\mu$J/per pulse for a minute exposure time the S/N can be improved by factor of $(60\times 10^4)^{0.5} \sim 770$. Furthermore, high repetition laser pulse rate can significantly reduce the peak power (energy) requirement of laser pulse for additional radiation safety consideration. There exists a vast choice of high repetitive femtosecond pulse lasers with tunable IR wavelength available, such as Ti-sapphire, semiconductors, YAG-dye lasers, etc.

3) Spatial Resolution as a Function of Laser Intensity

One factor which limits the x-ray technology to detect small hidden objects in vivo is the amount of radiation. The minimum spatial resolution is $x \sim 1/(I)^4$. The minimum dosage to detect 1-mm diameter hidden objects will require 10,000 times more than the dosage to detect 1-cm diameter hidden object. The threshold injury for the use of picosecond laser pulses directly illuminating the retina of monkeys in vivo was $\sim$2J/cm$^2$.

(4) Inhomogeneous Refractive Index

Due to the glandular, non-uniformity of breast tissue, the structure change of soft tissues masses from fat, water, and connective tissues of the breast, the spatial distribution of the refractive index across inhomogeneous turbid samples should be determined. Using ultrafast time gates, the variation of the refractive index, Nijk, to each voxel of a modeled sample and human organs can be measured using overlapped scanning approach. The inhomogeneous internal structure of the modeled turbid sample will be made by dividing the object into volume elements (voxels or pixels in 2-D ) and setting the size of the voxell to be the desired resolution. At each voxel (ijk): refractive index, absorption, forward scattering, sideward, and backward scattering coefficients are assumed. Within a voxel, particles are either absorbed or scattered to their nearest neighbors.

Using a high repetition rate ultrafast laser system, this single-ray probing/scanning approach can obtained in the spatial refractive index distribution with the mechanically map of the 2-D (i,j axes) plane and the time-gated k-axis. For example, a breast with dimension of $20\times 10^5$ cm$^3$ consists of 1,000,000 voxels with dimension of 1mm$^3$ each. Using a 100-MHz laser pulse repetition rate, $\sim$0.01 seconds are needed to take one complete scan of this sample. In order to improve the accuracy, $\sim$100 scans may be required for the signal averaging, wavelength dependence, and angular study. Theoretically, the measurement time is in the order of $\sim$ one second. Furthermore, the single ray scanning approach can reduce the peak power/energy requirement from the full beam imaging. The low power requirement can improve the laser safety from the overall operation.

Three computer-assisted methods for 3-D bailistic/-snake image reconstruction are disclosed for optical tomography to be used for the data analysis obtained from the time-gated optical imaging for future breast imaging. In all cases, the projection (illumination) source is an ultrashort laser pulses. Using an optical imaging system to compensate the shape distortion of the sphere, a sequence of time-delayed 2-D segmental plane images (ballistic and snake diffusive photons) can be detected with the Kerr gate and 2-D CCD camera. Using three different imaging systems from x-, y-, and z-projections and recording, a 3-D image can be reconstructed.

For a homogeneous sphere, the spatial distribution, index of refraction, and absorption coefficient can be deduced from the measured 2-D images For example, information of the dimensions (length, width height) and the index of refraction, n(r), can be extracted from the: time sequence of images (Ti−Tj) c/n(r)=ri−rj. By comparing the image intensity at different time: I(Ti)/I(Tj) =exp[(r) (-ri +rj)], the absorption coefficient can be obtained. These deductions are similar to x-ray tomography, except, an extra information of time (z-axis) has been obtained. For an inhomogeneous sample, extra images measured from different projection angles (see below) are required to reconstruct a 3-D image with unknown shapes index of refraction, and absorption coefficient.

The time-gated reflection optical tomography is similar to that of FIG. 14 and can be simpler for only one axis. However, disadvantages using reflection geometry are the difficulty to separate the input and reflected beams, the increase of absorption loss and scattering noise due to the doubling of optical path, and the necessity to use collection optics which increases the noise.

Three 3-D ballistic/snake image reconstruction methods are disclosed: (i) Time-gated "Single-Ray" optical tomography which adapts a similar approach to the conventional x-ray tomography; (ii) Ballistic/snake Steroscopic 3-D imaging; and (iii) Point-source fluorescence tomography.

The basic principle of computer-assisted tomography can be used in the 3-D ballistic/snake optical imaging system. The spatial distribution of the refractive index, absorption and scattering coefficients inside an inhomogeneous turbid sample can be determined from the measured ultrashort time gated images. At a cross-section of sample at Z=z1, the refractive index n(r,φ,z1), absorption coefficient (r,φ,z1), and scattering coefficient μs(r,φ,z1) are assumed. When a laser beam with the intensity input propagates through this cross-section of the sample, the wavefront of the laser beam will be distorted due to the inhomogeneity of n and the intensity of the output laser will be unevenly attenuated due to the fluctuation of α and μs. The output laser signal can be expressed as:

$$IT(r,\phi) = \int L \, N(R\phi)/c \, ds \quad (1a)$$

$$IE = \text{input} \exp(-\int L \times ds) \exp(-\int L \, \alpha a \, ds) \quad (1b)$$

where $\int \alpha ds = -\ln[IE/(\text{input} \exp(-\int L \, \alpha s \, ds)]$, IT and IE are measured values of delayed time and decay intensity of output ballistic signals, L is the optical path, ds is the differential length, and φ a parameter corresponding to the angular position in rotation. During the measurement, a rotation about a pre-selected origin would be carried out by M identical angle displacement steps, each of which is equal to πM. The varying of φ would be π/M, 2π/M, 3π/M, ... mπ/M, ..., π. For the variable of r in eq.1a, IT is the delay-time projection profile as a function of variable r: r1, r2, ..., rN at a particular angle φj=nπ/TM. This is shown in FIG.

Figure 17:
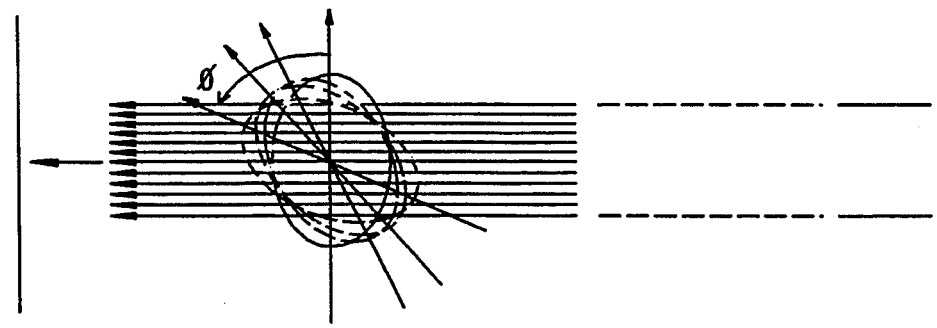
FIG. 17 is a schematic of Single-Ray Tomography to determine n and α at point P.

The absorption term of Iinput exp(−∫L αds) of eq.1b can be measured by the delayed-time- gated detection for the scattered light. The line integral of unknown distribution α(r,φ) is related to a determined value. A determination of unknown distribution n(r,φ) or α(r,φ) in a cross section region is equivalent to the determination of n and α at any point (r,φ). In the discrete- measurement, a point (r,φ) is replaced by a small domain with an identical area specified by (rp,φp) or (rp,φp) as shown in FIG. 17. To determine n or α at a point P(rp,φp), M line integrals are needed. Each integral which represents the propagation information at a particular angle mπ/M, has to pass the point (rp,φp). To obtain enough data to reconstruct the entire distribution of n and α at a z-plane, M step-rotation and N-beam illumination are needed. In a regular CAT, M~50 and N~20. In addition, eqs. 1a and 1b have assumed the laser pulse is a δ-function in the ballistic imaging.

After IT, IE have been obtained, the following 2-D Fourier transformation can be used to determine the unknown distributions n(r,φ) and α(r,φ). A general function q(x,y), which may represent either n(x,y) or α(x,y), can be written as:

$$q(x,y) = \int \int_{-\infty}^{\infty} Q(kx,ky) \exp[2\pi i(kxx + kyy)] \, dkxdky, \quad (2)$$

where kx and ky are the wave number in Kx-Ky Fourier plane and Q(kx/ky) is the Fourier transformation of a distribution function, q(x,y). Q(kx,ky) can be calculated as:

$$Q(kx,ky) = \int \int_{-\infty}^{\infty} q(x,y) \exp([2\pi i(kxx + kyy)] \, dxdy. \quad (3)$$

Figure 16:
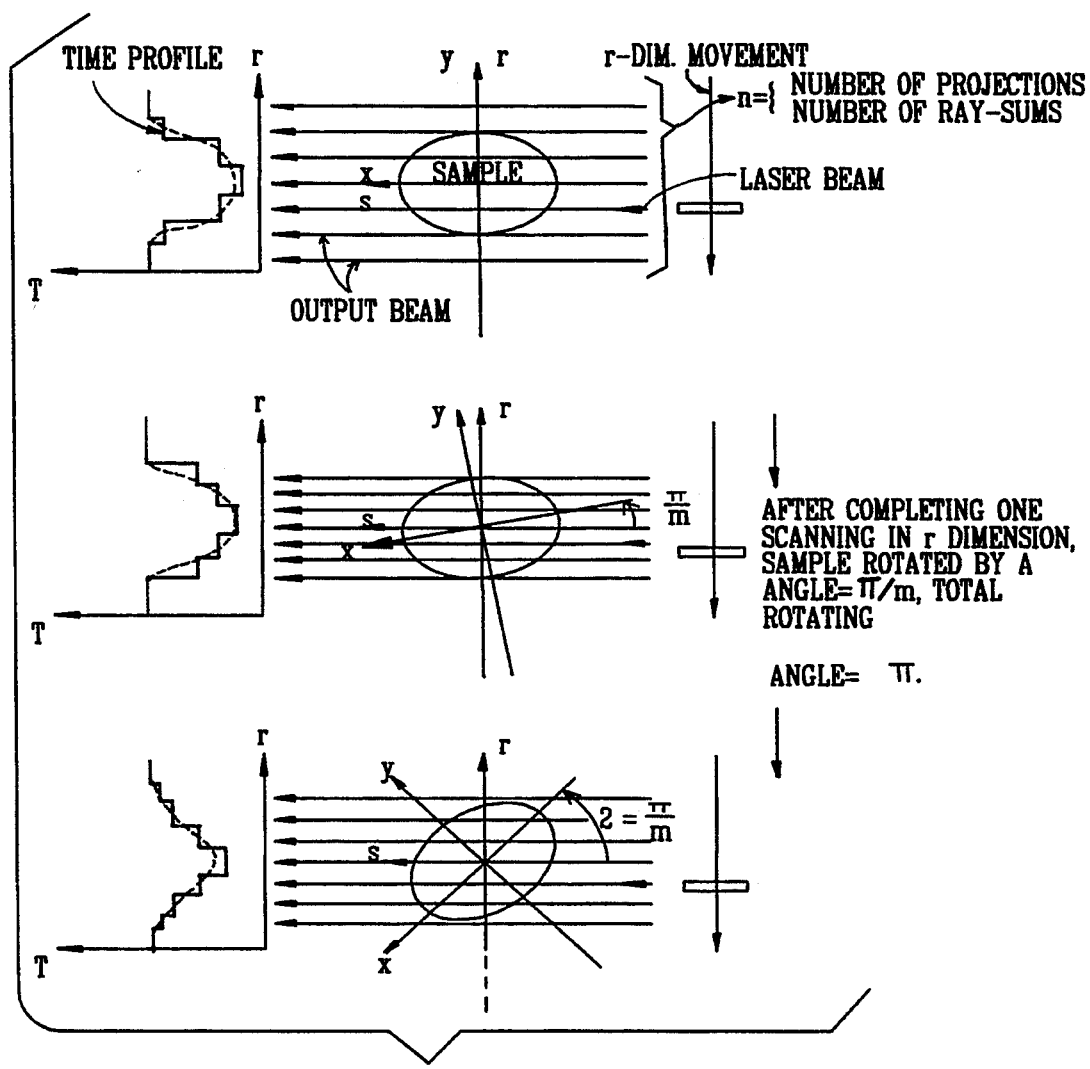
FIG. 16 are graphs useful in understanding the invention

The laboratory coordinate (r,s) as shown in FIG. 16, eq.3 can be transformed into the lab coordinate as:

$$Q(kx,ky) = \int \int_{-\infty}^{\infty} q(x,y) \exp(-2\pi ikr) \, drds = \quad (4)$$

$$\int_{-\infty}^{\infty} \left\{ \int_{-\infty}^{\infty} q(r,\phi) \, ds \right\} \exp(-2\pi ikr) \, dr,$$

φ=tan-1 (ky/kx) and k=(kx2+ky2)½. The inner integral in right hand side of eq.4 is simply the integral appearing in eq.1, that ∫n(r, φ/c ds or ∫α(r,φ) ds. Eq.4 can be written as:

$$Qn(kx,ky) = \int_{-\infty}^{\infty} IT(r,\phi) \exp(-2\pi ikr) \, dr, \quad (5a)$$

and $$Q(kx,ky) = -\int_{\infty\infty} IE(r,\phi) \exp(-2\pi ikr) \, dr. \quad (5b)$$

Eq.5 implies that once the measured data IT or IE, is obtained. the Fourier transformation of them with respect to r would be the 2-D Fourier transformation of the distribution n(x,y) or α(x,y) with respect to x and y, i.e. Qn(kx,ky) or Q (kx,ky). The inverse Fourier transformation of Qn or Qα can determine the unknown distributions n(x,y) or α(x,y) at a point (x,y).

To reconstruct the distribution of n(x,y) at point (x1,0) of a modeled system, a model system of a 2-D region with a uniform refractive index distribution except for a short piece of infinitesimal width. This k-φ Fourier plane is just a kx-ky plane as eq.5b implies. The inverse Fourier transformation of the 2-D function will provide the distribution function n(x,y).

A binocular stereosopic 3-D image can be constructed from two time-gated ballistic/snake signals. This method is simil. are in principle to human vision. A schematic diagram of binocular disparity is shown in FIG. 18. The views seen by two eyes are slightly different. A common feature, e.g. the front edge is imaged at corresponding points of the two retinas. Another feature of the left edge dD is imaged at locations on the two retinas that do not correspond to each other. The visual cortex of the brain will compare and analyze these similarities and disimilarities to determine the depth. The binocular disparity provides the depth information. Following the same approach, we can combined two 2-D ballistic/snake images measured at different angles with two video cameras in parallel processing (or one video camera in sequence processing) to reconstruct a 3-D image of hidden objects in turbid media using a computer software package or to display for directly eye viewing.

Figure 19:
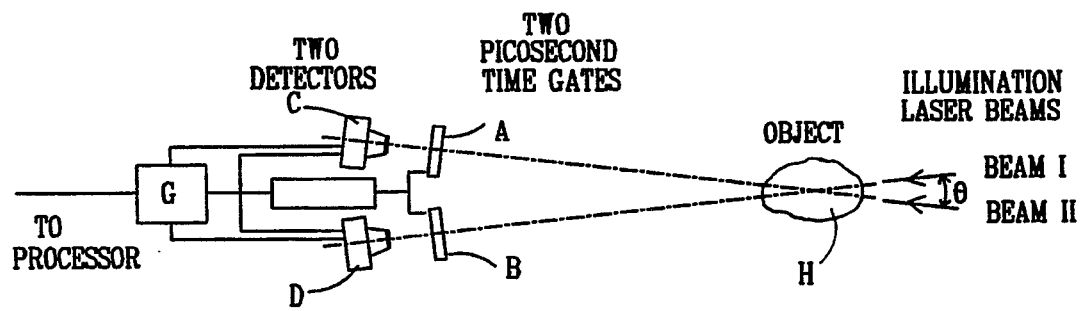
FIG. 19 is Time-Gated Sequential Stereoscopic 3-D Imaging.

A schematic of a controlled 3-D stereoscopic imaging is shown in FIG. 19. The object is illuminated by two independent probe .laser pulse beams: I and II, separated by an angle $\theta$. The transillumination images will be gated by two time gates A and B, then be recorded by two video cameras C and D. These two images which can be taken either in parallel or in sequence will be stored, and processed, and combined in a computer G. After that, The combined signal can be displayed into a 3-D stereoscopic image. For one camera approach, the video recording will be continuously switching back and forth between the two optical axes to record a sequencial disparity data for reconstruction..

Beside using a computer software package to reconstruct these two recorded 2-D disparity images and display a 3-D image. With a help of a pair of perpendicular polarized eyeglasses, we disclose two methods for balistic/snake 3-D stereoscopic eye viewing on a screen.

Figure 20:
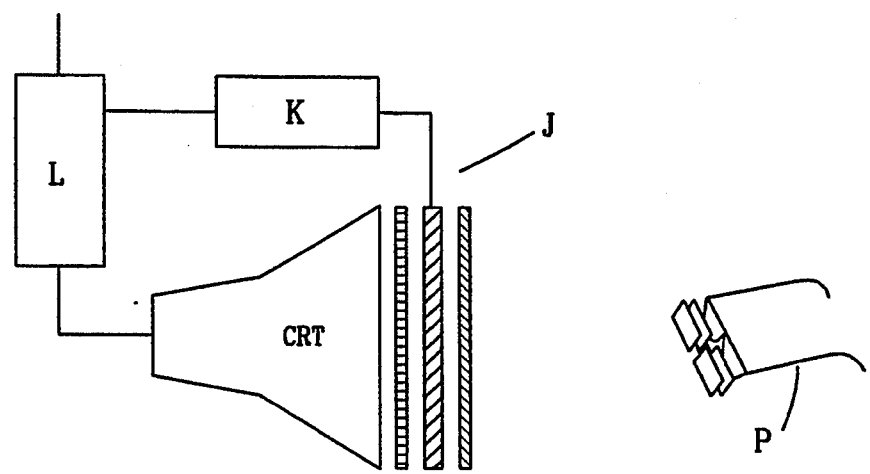
FIG. 20 is a 3-D Sequential Display.

(1) Sequential Display: As shown in FIG. 20, a electro-optical or mechanical shutter, J, is used to alternatively display two recorded ballistic/snake signals. The shutter is synchronized by a signal divider K of the two-video cameras C and D in (a) and which transmitted signals to a videodisplay CRT from a computer controller L. As long as the switching speed of the shutter is faster than the eye response (~30 Hz), these two sequence images received by a pair of perpendicular eyeglasses, P, will generated a pair of disparity images from beams I and II with different viewing angles and depth as shown in FIG. 18.

Figure 21:
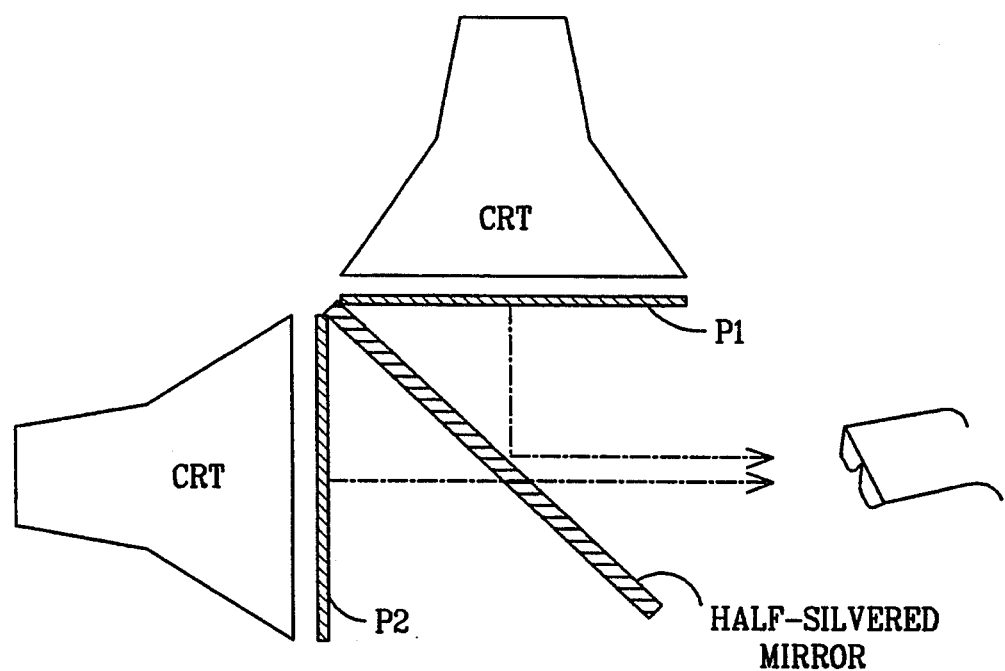
FIG. 21 is a 3-D Parallel Computer Display.

(2) Parellel Display As shown in FIG. 21, with two video display CRTs which display images recorded from cameras C and D, use a beam splitter and a pair of perpendicular polarized eyeglasses, two angular separated images can be viewed simultaneously by eyes for 3-D stereoscopic imaging.

Using polarization coding, two images obtained from two crossed polarized ballistic/snake trasnillumination images will be recorded, processed, and reconstructed. This ballistic/snake sterescopic 3-D imaging will help doctors, especially, surgeons to view the operation through video display with an additional depth information.

The signal to noise ratio of optical imaging can be further improved by using multiple wavelengths for probing and detecting growths inside organs in vivo. Fluorescence is commonly observed in tissues and biological samples with or without dyes. Preliminary results of point- source fluorescence imaging in modeled systems were discussed in section 2.A. In tissue samples, new wavelengths will be emitted from different fluophors at different locations of the sample. These fluorescence signals from different location will arrive at the 2-D Kerr imaging system at different times. Synchronizing the gating pulse, a particular plane can be imaged. Most noise from the incident wavelength can be removed from the Kerr image using color filters.

The analysis of a point-source fluorescence tomography is similar to seismic tomography, where shock waves are replaced by optical rays. In a first order approximation, the radius of the image, r, can be expressed as a function of delay time as $T = r^2/2V[1/(2o-2)^2 + 1/2^2]^{0.5}$ where zo is the ballistic distance (=0) and v is the group velocity. The reconstruction of images can be done using a random-walk approach by replacing parallel rays with spherical rays. The 3-D time-gated imaging system can be used to determine phantoms in turbid media and compare with the image reconstruction analysis. Images measured at the fluorescence wavelengths can be compared with the scattered images. The fluorescence emission spectra are different between cancer, benign, and normal tissues. This difference can be used for contrast to see an image in tissues.

Figure 22:
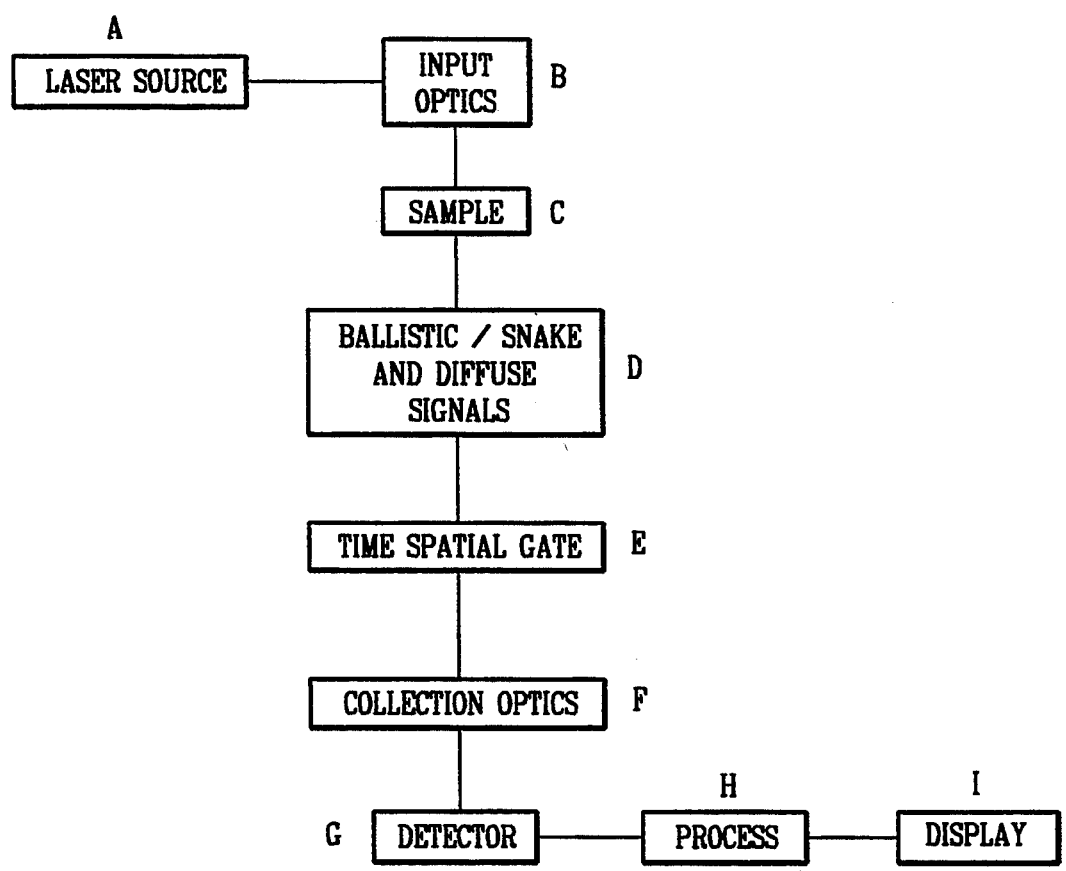
FIG. 22 is a block diagram of time-gated ballistic/-snake imaging and display.
Figure 23:
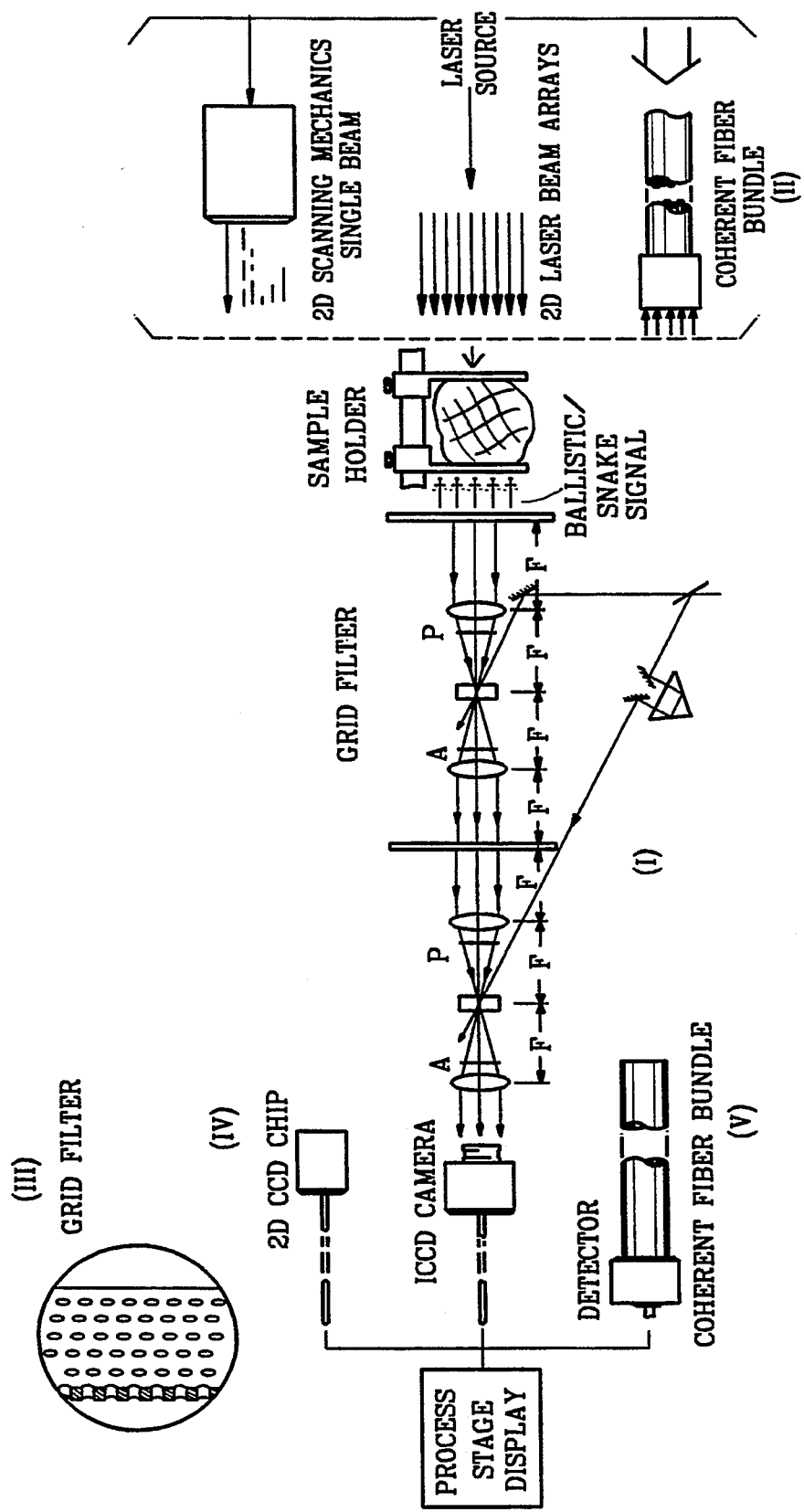
FIG. 23 is a schematic diagram of Instrumentation 4F Time-Gated System.
Figure 24:
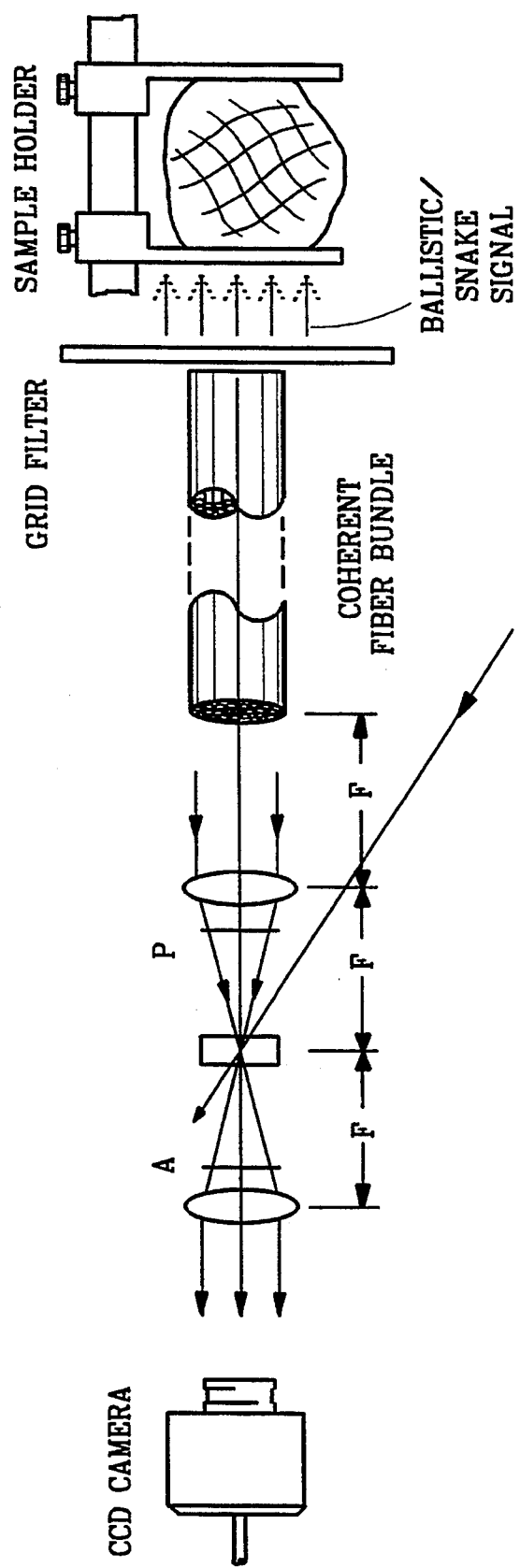
FIG. 24 is a Non-Scanning Illumination Time-Gated 2-D Imaging System

As can be seen, there are several important aspects of this invention. These aspects include the following: (a) the use of ultrafast time gates from optical and electronic means in the time domain of $10^{-10}$ to $10^{-14}$ seconds to image ballistic/snake early light signals. A block diagram of a complete system is displayed in FIG. 22. The time gate is <50-ps; (b) the use of ultrafast optical gates including optical Kerr gate, upper-conversion gate, phase-conjugation gate, and other nonlinear optical gates. Electronic gates include image intensifier and streak camera with <50-ps time resolution; (c) the use of a Fourier transformation and spatial aperture to modify spatial frequency at the Fourier plane of the time-gate to further filter late diffusive noise. See FIG. 12; (d) placing time-gate at the Fourier plane to select and modify image spatial frequencies of the early ballistic/snake light; (e) the use of laser field induced optical apertures for a means of the spatial aperture make out of a pin hole from a metal plate; (f) the use of two cascaded stage Kerr gates to couple with two Fourier spatial filters to image early ballistic/snake signals and remove late diffusive light. See FIG. 23-I; (g) the use of multiple (2 or more) time gates in sequences in conjunction with spatial filters to remove late diffusive noise. See FIG. 23-I. Each time gate is placed at the 2F Fourier places for time-space gating of ballistic/snake light; (h) the use of 4F Fourier spatial filtering to improve the image quality. Use zoom-lenses in the 4F Fourier imaging system shown in FIG. 23-I to compensate the thickness Variation of the sample; (i) the use of cooled 2-D video detectors to image ballistic/snake signals from 250-nm to 1100-nm; (j) the use of 2-D PtSi video detectors to image signals in the wavelength region of 1000-nm to 3000-nm; (k) using single ray scanning method to reconstruct the 3-D image from ballistic/snake signals; (l) the use of wavelength coding and time sequence coding to the single ray scanning 3-D imaging to improve the accuracy; (m) using imaging disparity (FIG. 18) through angular displacement from two 2-D ballistic/snake images to reconstruction 3-D stereographic image; (n) the use of angular coding in sequence (FIG. 20) or in parallel (FIG. 21) to introduce image disparity for the 2-D ballistic/snake images; (o) using either sequential or parallel polarization coding to display ballistic/snake 3-D steroscopic images; (p) using a fast processing/display (<0.05 seconds) and a slow processing/display (>0.1 seconds) video systems to image the ballistic/snake images. The fast display video system will provide a fast and rough image for the alignment and safety monitoring. The slow display video system will provide a long signal average for better sensitivity and accuracy. These two (slow and fast) imaging systems will obtain the transmitted ballistic/snake signals using optical beam splitter, mechanical mirror in and out, or electronic splitting from a video camera system; (q) the use of a time-gated imaging technique to distinguish cancer tissues from normal tissues using the differences of water concentration; (r) using multiple (greater than two) wavelengths in the wavelength region of 650-nm to 1500-nm (see FIG. 15) and differential absorption cross section to image the diseased tissues from the normal tissues, base on the concentrations of hemoglobin and water; (s) using a Forsterite laser with tunable wavelengths from 1150-nm to 1350-nm and Cr:YAG laser from 1300-nm to 1550-nm to identify the water concentration. Use mode-locked Ti:sapphire laser with tunable wavelength from 650-nm to 1000-nm to probe the concentrations of blood and other chromphores; (t) using high repetition rate and high scanning rate to reduce the photon fluence for safety radiation and to increase the signal averaging (u) the use of single coherent fiber bungle for single beam non-scanning illumination (FIG. 24) to acquire ballistic/snake images; (v) the use of single beam and opto-mechanical scanning method for 2-D mapped illumination (FIG. 23-II) to acquire ballistic/snake images; (w) using a multiple beam for 2-D non-scanning illumination (FIG. 23-II); (x) using equal-optical-path optical collection system (FIG. 23-I) to acquire time-gated transilluminated signals; (y) using grid filtering (FIG. 23-III) to collect time-gated signals; (z) the use of collimator arrays (FIG. 23-I) to collect time-gated signals; (aa) the use of high repetition rate laser sources and a high speed frame grabber for 2-D and 3-D real time display; (bb) using a video cassette recorder for massive analog 2-D ballistic/snake image recording and storage; (cc) the use of 2-D coherent-fiber-CCD assembly (FIG. 23-V) for directly 2-D and 3-D time-gated ballistic imaging; (dd) using color-filtered time-gated signals for computer aided medical analysis; (ee) diagnosing diseases using time-gated imaging, e.g. breast cancer screening, cholesterol concentration in blood vessels in vivo, blood vessel clogging, oxygen concentration in blood vessel, gum disease, etc.; (ff) diagnosing silicone leakage from the breast implantation.

What is claimed is

1. A system for imaging an object in or behind a highly scattering medium comprising:
    a) means for illuminating said highly scattering medium with a beam of light, the light emerging therefrom consisting of a ballistic component, a snake-like component and a diffuse component, and
    b) means for forming a temporally gated image of the light passed through, the temporally gated image consisting mainly of the ballistic component and the snake-like component and not the diffuse component, said means including a lens and Kerr gate.

2. A method for imaging an object in or behind a highly scattering medium comprising:
    a) illuminating said highly scattering medium with a beam of light, the light emerging therefrom consisting of a ballistic component, a snake-like component and a diffuse component, and
    b) forming a temporally gated image of the light passed through using a lens and a Kerr gate, the temporally gated image consisting mainly of the ballistic component and the snake-like component and not the diffuse component.

3. A system for imaging an object in or behind a highly scattering medium comprising:
    a) means for illuminating said highly scattering medium with a beam of light, the light emerging therefrom consisting of a ballistic component, a snake-like component and a diffuse component, and
    b) means for forming a temporally and spacially gated image of the light passed through, the temporally gated image consisting mainly of the ballistic component and the snake-like component and not the diffuse component, said means including a 4F Fourier spatial gate and a Kerr type time gate.

4. A method of obtaining a 2-dimensional image of an object in or behind a highly scattering medium, said method comprising the steps of:
    a) illuminating the entire object at once through said highly scattering medium with a beam of light, the light emerging from said highly scattering medium consisting of a ballistic component, a snake-like component and a diffuse component;
    b) simultaneously temporally and spatially gating the emergency light to selectively pass said ballistic component and said snake-like component; and
    c) forming a 2-dimensional image of the temporally and spatially gated light.

5. The method as claimed in the claim 4 wherein said illuminating step comprises illuminating the object through the highly scattering medium with near IR light.

6. A system for obtaining a 2-dimensional image of an object in or being a highly scattering medium, said system comprising:
    a0 means for illuminating the object all at once through said highly scattering medium with a beam of light, the light emerging from said highly scattering medium consisting of a ballistic component, a snake-like component and a diffuse component;
    b) means for simultaneously temporally and spatially gating the emergent light to selectively pass said ballistic component and said snake-like component; and
    c) means for forming a 2-dimensional image of the temporally and spatially gated light.

7. The system as claimed in claim 6 wherein said gating means comprises a Kerr gate positioned at a 2F spectral plane.

8. The system as claimed in claim 6 wherein said gating means comprises two or more Kerr gates arranged in series, each Kerr gate being positioned at a 2F spectral plane.

9. A system for obtaining a 3-dimensional image of an object in or behind a highly scattering medium, said system comprising:

a) means for illuminating the object through said highly scattering medium with a first beam of light and a second beam of light, said first beam of light and said second beam of light illuminating the object through said highly scattering medium at different angles, the light emerging from said highly scattering medium from each of said first and said second beams of light consisting of a ballistic component, a snake-like component and a diffuse component;

b) first gating means for gating the emergency light from said highly scattering medium attributable to said first beam so as to selectively pass said ballistic component and said snake-like component thereof;

c) second gating means for gating the emergent light from said highly scattering medium attributable to said second beam so as to selectively pass said ballistic component and said snake-like component thereof;

d) first imaging means for forming a 2-dimensional image of the gaged light from said first beam;

e) second imaging means for forming a 2-dimensional image of the gated light from said second beam; and f) processing means for forming a 3-dimensional image using said 2-dimensional images from said first beam and said second beam

* * * * *